United States Patent [19]

Macor

[11] Patent Number: 5,498,626
[45] Date of Patent: Mar. 12, 1996

[54] ACYLAMINOINDOLE DERIVATIVES AS 5-HT1 AGONISTS

[75] Inventor: John E. Macor, Salem, Conn.

[73] Assignee: Pfizer Inc., New York, N.Y.

[21] Appl. No.: 295,792

[22] PCT Filed: Mar. 4, 1993

[86] PCT No.: PCT/US93/01807

§ 371 Date: Sep. 14, 1994

§ 102(e) Date: Sep. 14, 1994

[87] PCT Pub. No.: WO93/21180

PCT Pub. Date: Oct. 25, 1993

Related U.S. Application Data

[63] Continuation-in-part of Ser. No. 866,382, Apr. 10, 1992, abandoned.

[51] Int. Cl.[6] .................. C07D 403/06; C07D 403/14; A61K 31/40
[52] U.S. Cl. .................. 514/414; 514/323; 514/397; 546/201; 548/468; 548/312.1
[58] Field of Search .................. 514/323, 414, 514/397; 546/201; 548/468, 312.1

[56] References Cited

U.S. PATENT DOCUMENTS

| | | | |
|---|---|---|---|
| 4,252,803 | 2/1981 | Webb | 424/248.5 |
| 4,839,377 | 6/1989 | Bays et al. | 514/415 |
| 4,855,314 | 8/1989 | Oxford et al. | 514/415 |
| 5,208,248 | 5/1993 | Baker et al. | 514/364 |
| 5,298,491 | 3/1994 | Chauveau | 514/17 |

FOREIGN PATENT DOCUMENTS

| | | |
|---|---|---|
| 0303506 | 8/1988 | European Pat. Off. |
| 0313397 | 10/1988 | European Pat. Off. |
| 0354777 | 8/1989 | European Pat. Off. |
| 0438230 | 7/1991 | European Pat. Off. |
| 0497512 | 8/1992 | European Pat. Off. |
| 9118897 | 12/1991 | WIPO |

OTHER PUBLICATIONS

W. Feniuk, et al., P. P. A. Humphrey & M. J. Perren–Br. J. Pharmacol. (1989), 96, 83–90.
P. P. A. Humphrey, et al.–Br. J. Pharmacol. (1988), 94, 1123–1132.
R. E. Hearing et al. J. Neuroscience, 7, 894 (1987).

*Primary Examiner*—Jacqueline Haley
*Attorney, Agent, or Firm*—Peter C. Richardson; Paul H. Ginsburg; Grover F. Fuller, Jr.

[57] ABSTRACT

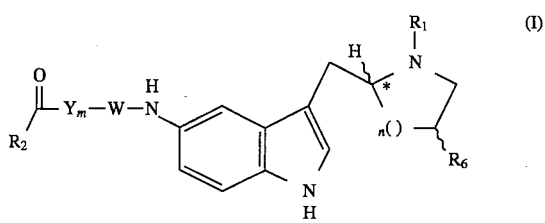

Compounds of formula (I) where n is 0, 1, or 2; m is 0 or 1; Y and W are each an amino acid residue; $R_1$ is hydrogen, $C_1$–$C_6$ alkyl, $C_3$–$C_6$ alkenyl, $C_3$–$C_6$ alkynyl, aryl, $C_1$–$C_3$ alkylaryl, or $C_1$–$C_3$ alkylheteroaryl, and —$(CH_2)_pR_3$; $R_2$ is $CF_3$, $C_1$–$C_6$ alkyl, aryl, $C_1$–$C_3$ alkylaryl, and —$OR_5$; $R_3$ is cyano, trifluoromethyl, or —$OR_4$; $R_4$ is hydrogen, $C_1$–$C_6$ alkyl, $C_1$–$C_3$ alkylaryl, or aryl; $R_5$ is $C_1$–$C_6$ alkyl, $C_1$–$C_3$ alkylaryl, or aryl; $R_6$ is hydrogen, —$OR_7$, or —$NHCOR_7$; $R_7$ is hydrogen, $C_1$ to $C_6$ alkyl, aryl or $C_1$ to $C_3$ alkyl-aryl; p is 1, 2, or 3; and the above aryl groups and the aryl moieties of the above alkyl-aryl groups are independently selected from phenyl and substituted phenyl, wherein said substituted phenyl may be substituted with one to three groups selected from $C_1$ to $C_4$ alkyl, halogen, hydroxy, cyano, carboxamide, nitro, and $C_1$ to $C_4$ alkoxy and the pharmaceutically acceptable salts thereof. These compounds are useful in treating migraine and other disorders. These compound are useful psychotherapeutics and are potent serotonin (5-HT$_1$) agonists and may be used in the treatment of depression, anxiety, eating disorders, obesity, drug abuse, cluster headache, migraine, pain, and chronic paroxysmal hemicrania and headache associated with vascular disorders, and other disorders arising from deficient serotonergic neurotransmission. The compounds can also be used as centrally acting antihypertensives and vasodilators.

23 Claims, No Drawings

ACYLAMINOINDOLE DERIVATIVES AS 5-HT1 AGONISTS

This application is a National Stage application of PCT/US93/01807, now WO93/21180 published Oct. 28, 1993 which is a Continuation-in-Part of U.S. Ser. No. 07/866,382 filed Apr. 10, 1992, now abandoned.

BACKGROUND OF THE INVENTION

The present invention relates to indole derivatives, to processes and intermediates for their preparation, to pharmaceutical compositions containing them and to their medicinal use. The active compounds of the present invention are useful in treating migraine and other disorders.

U.S. Pat. Nos. 4,839,377 and 4,855,314 and European Patent Application Publication No. 313397 refer to 5-substituted 3-aminoalkyl indoles. The compounds are said to be useful for the treatment of migraine.

British Patent Application 040279 refers to 3-aminoalkyl-1H-indole-5-thioamides and carboxamides. The compounds are said to be useful in treating hypertension, Raymond's disease and migraine.

European Patent Application Publication No. 303506 refers to 3-poly:hydro-pyridyl-5-substituted-1H-indoles. The compounds are said to have 5-$HT_1$ receptor agonist and vasoconstrictor activity and to be useful in treating migraine.

European Patent Application Publication No. 354777 refers to N-piperidinyl:indolyl:ethyl-alkane sulfonamide derivatives. The compounds are said to have 5-$HT_1$ receptor agonist and vasoconstrictor activity and to be useful in treating cephalic pain.

European Patent Applications Publication Numbers 438230, 494774, and 497512 refers to indole-substituted five-membered heteroaromatic compounds. The compounds are said to have 5-$HT_1$-like receptor agonist activity and to be useful in the treatment of migraine and other disorders for which a selective agonist of these receptors is indicated.

International Patent Application PCT/GB91/00908 and European Patent Application No. 313397A refers to 5-heterocyclic indole derivatives. The compounds are said to exhibit properties useful in the treatment and prophylaxis of migraine, cluster headache, and headache associated with vascular disorders. These compounds are also said to have "5-$HT_1$-like" receptor agonism.

European Patent Application Publication No. 457701 refers to certain aryloxyamine derivatives as having a high affinity for 5-$HT_{1D}$ serotonin receptors. These compounds are said to be useful in treating diseases related to 5-HT receptor disfunction, especially migraine.

SUMMARY OF THE INVENTION

The present invention relates to compounds of the formula

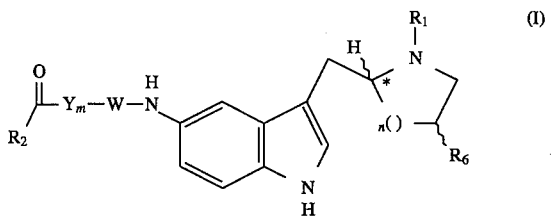

where n is 0, 1, or 2; m is 0 or 1; Y and W are each an amino acid residue (including naturally occurring amino acids such as alanine, valine, leucine, isoleucine, proline, phenylalanine, tryptophan, methionine, glycine, serine, threonine, cysteine, tyrosine, asparginine, glutamine, aspartic acid, glutamic acid, lysine, arginine, or histidine); $R_1$ is hydrogen, $C_1$-$C_6$ alkyl, $C_3$-$C_6$ alkenyl, $C_3$-$C_6$ alkynyl, aryl, $C_1$-$C_3$ alkylaryl, or $C_1$-$C_3$ alkylheteroaryl, and —$(CH_2)_p R_3$; $R_2$ is $CF_3$, $C_1$-$C_6$ alkyl, aryl, $C_1$-$C_3$ alkylaryl, and —$OR_5$; $R_3$ is cyano, trifluoromethyl, or —$OR_4$; $R_4$ is hydrogen, $C_1$-$C_6$ alkyl, $C_1$-$C_3$ alkylaryl, or aryl; $R_5$ is $C_1$-$C_6$ alkyl, $C_1$-$C_3$ alkylaryl, or aryl; $R^6$ is hydrogen, —$OR_7$, or —$NHCOR_7$; $R_7$ is hydrogen, $C_1$ to $C_6$ alkyl, aryl, or $C_1$ to $C_3$ alkyl-aryl; p is 1, 2, or 3; and the above aryl groups and the aryl moieties of the above alkyl-aryl groups are independently selected from phenyl and substituted phenyl, wherein said substituted phenyl may be substituted with one to three groups selected from $C_1$ to $C_4$ alkyl, halogen (e.g. fluorine, chlorine bromine or iodine), hydroxy, cyano, carboxamide, nitro, and $C_1$ to $C_4$ alkoxy and the pharmaceutically acceptable salts thereof. These compounds are useful in treating migraine and other disorders.

The compounds of the invention include all optical isomers of formula I (e.g., R and S stereogenicity at any chiral site) and their racemic, diastereomeric, or epimeric mixtures. When $R_6$ is hydrogen, the epimers with the R absolute configuration at the chiral carbon site designated by an asterisk in formula I are preferred. When $R_6$ is —$OR_7$ or —$NHCOR_7$ and n is O or 1, the epimers with the S absolute configuration at the chiral carbon site designated by an asterisk in formula I are preferred. When $R_6$ is —$OR_7$ or —$NHCOR_7$ and n is 2, the epimers with the R absolute configuration at the chiral carbon site designated by an asterisk in formula I are preferred. When $R_6$ is —$OR_7$ or —$NHCOR_7$ and n is O, the cis epimers [(2S, 3S) absolute configuration in the azetidine ring] are particularly preferred. When $R_6$ is —$OR_7$ or —$NHCOR_7$ and n is 1, the cis epimers [(2S, 4R) absolute configuration in the pyrrolidine ring] are particularly preferred. When $R_6$ is —$OR_7$ or —$NHCOR_7$ and n is 2, the cis epimers [(2R, 5R) absolute configuration in the piperidine ring] are particularly preferred.

Unless otherwise indicated, the alkyl, alkenyl, and alkynyl groups referred to herein, as well as the alkyl moieties of other groups referred to herein (e.g. alkoxy), may be linear or branched, and they may also be cyclic (e.g. cyclopropyl, cyclobutyl, cyclopentyl, or cyclohexyl) or be linear or branched and contain cyclic moieties.

Preferred compounds of the invention are compounds of the formula I wherein n is 1; m is 0; the amino acid is a naturally occurring amino acid; $R_1$ is hydrogen, $C_1$-$C_4$ alkyl, or —$CH_2CH_2OCH_3$; is $C_{-C4}$ alkyl, —Ph (Ph=phenyl), —$CF_3$, or —$OR_5$. Of the foregoing preferred compounds, when $R_6$ is hydrogen, the epimers with the R absolute configuration at the chiral carbon site designated by an asterisk in formula I are more preferred. Of the foregoing preferred compounds, when $R_6$ is —$OR_7$ or —$NHCOR_7$, the epimers with the S absolute configuration at the chiral carbon site designated by an asterisk in formula I are more preferred. Of the foregoing compounds, when $R_6$ is —$OR_7$ or —$NHCOR_7$, the cis epimers [(2S, 4R) absolute configuration in the pyrrolidine ring] are particularly preferred.

The following compounds are particularly preferred:

5-(N-benzyloxycarbonylglycyl)amino-3-(N-methylpyrrolidin- 2-(R)-ylmethyl)-1H-indole;

5-(N-benzyloxycarbonyl-(S)-histidyl)amino-3-(N-methylpyrrolidin- 2-(R)-ylmethyl)-1H-indole;

5-(N-benzyloxylcarbonyl-(S)-phenylalanyl)amino-3-(N-methylpyrrolidin- 2R-ylmethyl)-1H-indole; and 5-(N-benzyloxycarbonyl-(S)-alanyl)amino-3-(N-methylpyrrolidin-2-(R)-ylmethyl)-1H-indole.

The present invention also relates to a compound of the formula

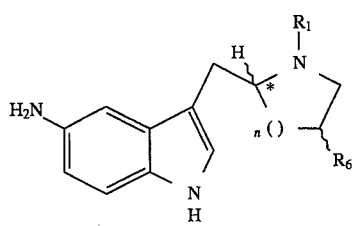

II where n is 0, 1, or 2; $R_1$ is hydrogen, $C_1$–$C_6$ alkyl, $C_3$–$C_6$ alkenyl, $C_3$–$C_6$ alkynyl, aryl, $C_1$–$C_3$ alkylaryl, or $C_1$–$C_3$ alkylheteroaryl, and —$(CH_2)_pR_3$; $R_3$ is cyano, trifluoromethyl, or —$OR_4$; $R_4$ is hydrogen, $C_1$–$C_6$ alkyl, $C_1$–$C_3$ alkylaryl, or aryl; $R_6$ is hydrogen, —$OR_7$, or —$NHCOR_7$; $R_7$ is hydrogen, $C_1$ to $C_6$ alkyl, aryl, or $C_1$ to $C_3$ alkyl-aryl; p is 1, 2, or 3; a chiral carbon is designated by as asterisk; and the above aryl groups and the aryl moieties of the above alkyl-aryl groups are independently selected from phenyl and substituted phenyl, wherein said substituted phenyl may be substituted with one to three groups selected from $C_1$ to $C_4$ alkyl, halogen (e.g. fluorine, chlorine bromine or iodine), hydroxy, cyano, carboxamide, nitro, and $C_1$ to $C_4$ alkoxy. When $R_6$ is hydrogen, the epimers with the R absolute configuration at the chiral carbon site designated by an asterisk in formula II are preferred. When $R_6$ is —$OR_7$ or —$NHCO_7$ and n is O or 1, the epimers with the S absolute configuration at the chiral carbon site designated by an asterisk in formula II are preferred. When $R_6$ is —$OR_7$ or —$NHCOR_7$ and n is 2, the epimers with the R absolute configuration at the chiral carbon site designated by an asterisk in formula II are preferred. When $R_6$ is —$OR_7$ or —$NHCOR_7$ and n is O, the cis epimers [(2S, 3S) absolute configuration in the azetidine ring] are particularly preferred. When $R_6$ is —$OR_7$ or —$NHCOR_7$ and n is 1, the cis epimers [(2S, 4R) absolute configuration in the pyrrolidine ring] are particularly preferred. When $R_6$ is —$OR_7$ or —$NHCOR_7$ and n is 2, the cis epimers [(2R, 5R) absolute configuration in the piperidine ring] are particularly preferred. These compounds are useful as intermediates in preparing compounds of formula I.

The present invention also relates to a pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an amount of a compound of the formula I or a pharmaceutically acceptable salt thereof effective in treating such condition and a pharmaceutically acceptable carrier.

The present invention also relates to a method for treating a condition selected from hypertension, depression, anxiety, eating disorders, obesity, drug abuse, cluster headache, migraine, pain and chronic paroxysmal hemicrania and headache associated with vascular disorders comprising administering to a mammal (e.g., a human) requiring such treatment an amount of the formula I or a pharmaceutically acceptable salt thereof effective in treating such condition.

The present invention also relates to a pharmaceutical composition for treating disorders arising from deficient serotonergic neurotransmission (e.g., depression, anxiety, eating disorders, obesity, drug abuse, cluster headache, migraine, pain and chronic paroxysmal hemicrania and headache associated with vascular disorders) comprising administering to a mammal (e.g., a human) requiring such treatment an amount of a compound of the formula I or a pharmaceutically acceptable salt thereof effective in treating such condition.

The present invention also relates to a method for treating disorders arising from deficient serotonergic neurotransmission (e.g., depression, anxiety, eating disorders, obesity, drug abuse, cluster headache, migraine, pain and chronic paroxysmal hemicrania and headache associated with vascular disorders) comprising administering to a mammal (e.g., a human) requiring such treatment an amount of a compound of the formula I or a pharmaceutically acceptable salt thereof effective in treating such condition.

DETAILED DESCRIPTION OF THE INVENTION

The compounds of the present invention can be prepared as shown in the following reaction scheme:

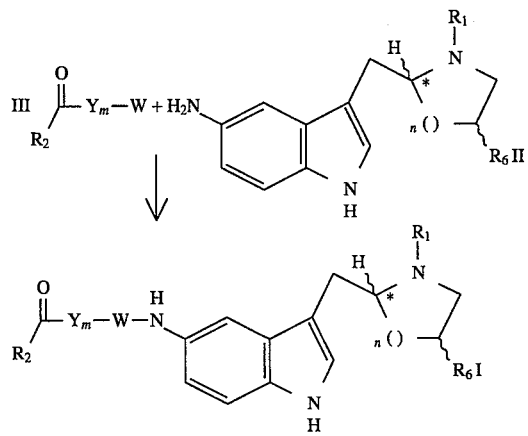

Compounds of formula I are prepared by the coupling reaction of a compound of formula II where n, $R_1$, and $R_6$ are as defined above with a compound of the formula III where m, $R_2$, Y, and W are as defined above with Y and W having a C terminal on the right side and an N terminal on the left side of each residue, the C terminal of W being in the carboxylic acid form. The reaction is carried out in the presence of a carboxylic acid activating agent in an inert solvent. Suitable carboxylic acid activating agents include oxalyl chloride, thionyl chloride, carbonyldiimidazole, dicyclohexylcarbodiimide, and 1-ethyl-3-(3-dimethylaminopropyl)-carbodiimide. The preferred carboxylic acid activating agent is carbonyldiimidazole. Suitable solvents include diethyl ethyl, tetrahydrofuran, 1,4-dioxane, chloroform, methylene chloride, or N,N-dimethylformamide. The preferred solvent is methylene chloride. The reaction is run at a temperature of from about 0° C. to about 65° C., preferably at about 25° C. (room temperature).

Compounds of the formula III are either commercially available or can be prepared using methods known in the art, for example, as described in M. Bodanszky, *Peptide Synthesis*, John Wiley and Sons, New York (1976).

Compounds of formula II can be prepared as shown in the following reaction scheme:

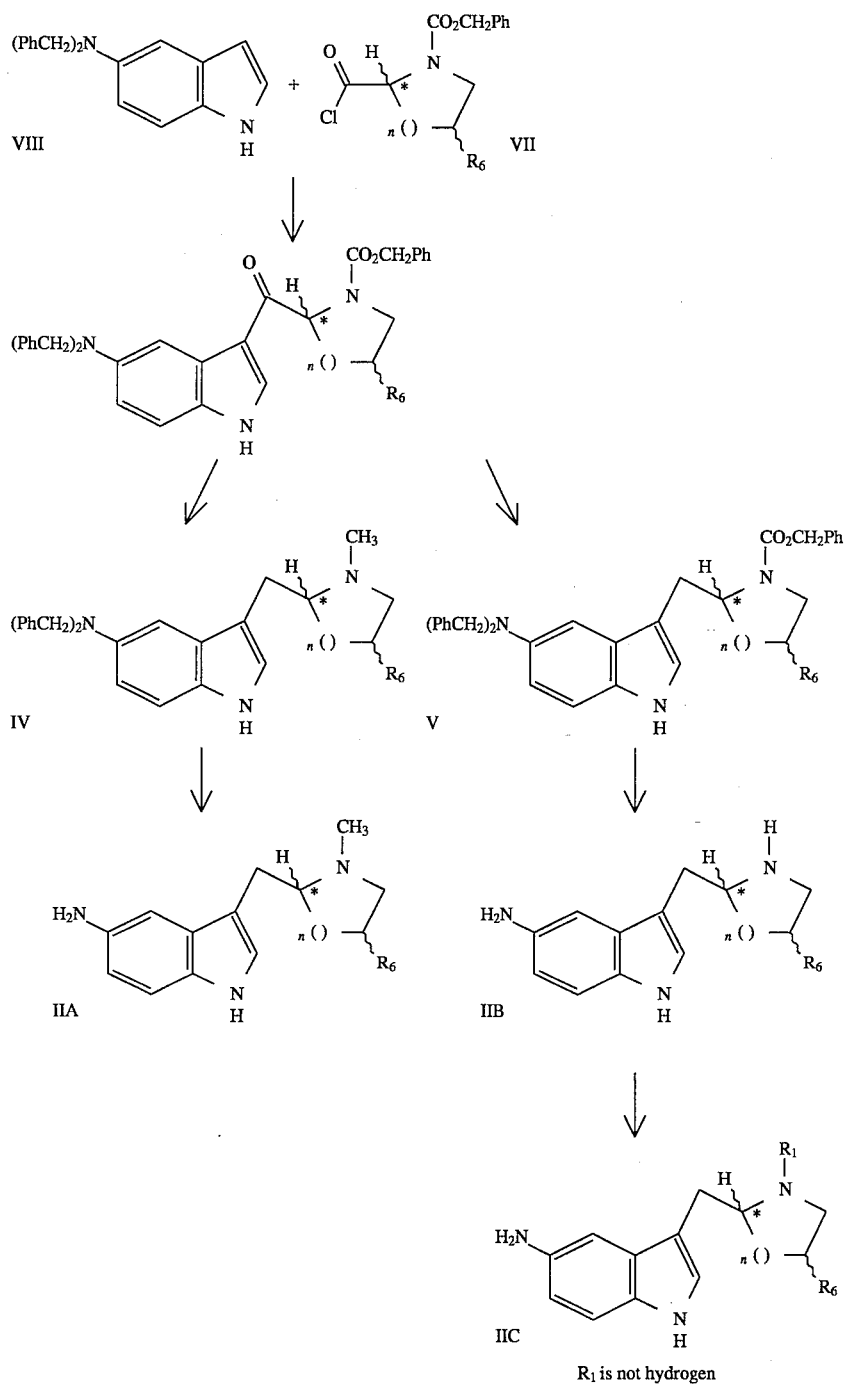

R₁ is not hydrogen

Compounds of formula IIC where n and $R_6$ are as defined above and $R_1$ is as defined above but for hydrogen are prepared by the alkylation of a compound of formula IIB where n and $R_6$ are as defined above with an alkylating agent and a base in an inert solvent. Suitable alkylating agents include alkyl halides (chlorides, bromides, or iodides), alkyl tosylates, alkyl mesylates, alkyl triflates, α, β-unsaturated ketones, α, β-unsaturated esters, α, β-unsaturated aldehydes, α, β-unsaturated amides, and α, β-unsaturated nitriles. Alkyl halides (iodides) are preferred. Suitable solvents include methylene chloride, chloroform, carbon tetrachloride, acetonitrile, tetrahydrofuran, diethyl ether, dioxane, N,N-dimethylformamide, ethanol, propanol, methanol. The preferred solvent is acetonitrile. The reaction is conducted between a temperature of about 0° C. to about 150° C. preferably about 0° C. to about 25° C.

Compounds of formula IIA where n and $R_6$ are as defined above are prepared by catalytic reduction of a compound of formula IV where n and $R_6$ are as defined above under an atmosphere of hydrogen, preferably at a pressure of about 1 to about 3 atmospheres, or using a hydrogen source such as ammonium formate or formic acid in an inert solvent. Suitable catalysts include palladium on carbon, palladium hydroxide on carbon, Raney nickel, and platinum oxide. The preferred catalyst is palladium hydroxide on carbon. Suitable solvents include $C_1$ to $C_6$ alcohols, N,N-dimethylformamide, ethyl acetate, and acetonitrile. The preferred solvent is ethanol. The reaction is conducted at a temperature of about 0° C. to about 100° C., most preferably at about 50° C.

Compounds of formula IIB where n and $R_6$ are as defined above are prepared by catalytic reduction of a compound of the formula V where n and $R_6$ are as defined above under an atmosphere of hydrogen, preferably at a pressure of about 1 to about 3 atmospheres, or using a hydrogen source such as ammonium formate or formic acid in an inert solvent. Suitable catalysts include palladium on carbon, palladium hydroxide on carbon, Raney nickel, and platinum oxide. The preferred catalyst is palladium hydroxide on carbon. Suitable solvents include $C_1$ to $C_6$ alcohols, N,N-dimethylformamide, ethyl acetate, and acetonitrile. The preferred solvent is ethanol. The reaction is conducted at a temperature of about 0° C. to about 100° C., most preferably at about 50° C.

Compounds of formula IV are prepared via the hydride reduction of a compound of the formula VI using methods known in the art, for example, as described in W. A. Reimers, "Indole Aldehydes and Ketones" in the series *The Chemistry of Heterocyclic Compounds*, Volume 25, Part III, Weissberger, A. and Taylor, E. C. (eds), John Wiley and Sons, New York, pp. 403–405 (1979).

Compounds of formula V are prepared via the hydride reduction of a compound of the formula VI using methods known in the art, for example, as described in W. A. Reimers, "Indole Aldehydes and Ketones" in the series *The Chemistry of Heterocyclic Compounds*, Volume 25, Part III, Weissberger, A. and Taylor, E. C. (eds), John Wiley and Sons, New York, pp. 403–405 (1979).

Compounds of formula VI are prepared using methods known in the art, for example, as described in W. A. Reimers, "Indole Aldehydes and Ketones" in the series *The Chemistry of Heterocyclic Compounds*, Volume 25, Part III, Weissberger, A. and Taylor, E. C. (eds), John Wiley and Sons, New York, pp. 388–389 (1979).

Compounds of the formula VII are using prepared methods known in the art, for example, as described in Aoyama, T. and Shioiri, T., *Chem. Pharm. Bull*, 3249 (1981). Other halogens can be used in place of chloride in formula VII and are prepared using methods known in the art, however, chloride is preferred.

Compounds of formula VIII are prepared using methods known in the art, such as, for example, as disclosed in Example 8.

The —$CO_2CH_2Ph$ group in compound of formula VII and the $PhCH_2$— groups in compound of formula VIII are protecting groups for the nitrogen atoms in each of the respective compounds and are preferred. Other protecting groups include —$COCF_3$, —$COCH_2CCl_3$, —$CO_2C(CH_3)_3$ and —$CH_2OCH_2Ph$. Compounds of formulae VII and VIII having these other protecting groups can be prepared using methods known in the art. Removal of these other protecting groups to form compounds of formulae IIA, IIB and IV can also be accomplished using methods known in the art, for example, as described in T. W. Greene, *Protecting Groups in Organic Synthesis*, John Wiley and Sons, New York (1981), pp. 218–287.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, i.e., where W contains a carboxylate, are capable of forming base salts with various pharmacologically acceptable cations. Examples of such salts include the alkali metal or alkaline-earth metal salts and particular, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium, magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction of maximum product of yields of the desired final product.

The compounds of the formula I and the pharmaceutically acceptable salts thereof (hereinafter, also referred to as the active compounds of the invention) are useful psychotherapeutics and are potent serotonin (5-$HT_1$) agonists and may be used in the treatment of depression, anxiety, eating disorders, obesity, drug abuse, cluster headache, migraine, chronic paroxysmal hemicrania and headache associated with vascular disorders, pain, and other disorders arising from deficient serotonergic neurotransmission. The compounds can also be used as centrally acting antihypertensives and vasodilators. The active compounds of the invention can be evaluated as antimigraine agents by testing the extent to which they mimic sumatriptan in contracting the dog isolated saphenous vein strip [P.P.A. Humphrey et al., *Br. J. Pharmacol.*, 94, 1128 (1988)]. This effect can be blocked by methiothepin, a known serotonin antagonist. Sumatriptan is known to be useful in the treatment of migraine and produces a selective increase in carotid vascular resistance in the anesthetized dog. It has been suggested [W. Fenwick et al., *Br. J. Pharmacol.*, 96, 83 (1989)] that this is the basis of its efficacy.

The serotonin 5-$HT_1$ agonist activity is measured in in vitro receptor binding assays as described for the 5-$HT_{1A}$ receptor using rat cortex as the receptor source and [³H]-8-OH-DPAT as the radioligand [D. Hoyer et al. *Eur. J. Pharm.*, Vol. 118, 13 (1985)] and as described for the 5-HT$_{1D}$ receptor using bovine caudate as the receptor source and [³H] serotonin as the radioligand [R. E. Heuring and S. J. Peroutka, *J. Neuroscience*, Vol. 7, 894 (1987)]. 5-HT$_1$ agonist activity is defined by agents with affinities (IC$_{50}$) of 250 nM or less with either binding assay.

The compositions of the present invention may be formulated in a conventional manner using one or more pharmaceutically acceptable carriers. Thus, the active compounds of the invention may be formulated for oral, buccal, sublingual, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinized maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal and sublingual administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., migraine) is 0.1 to 200 mg of the active ingredient per unit dose which could be administered, for example, 1 to 4 times per day.

Aerosol formulations for treatment of the conditions referred to above (e.g., migraine) in the average adult are preferably arranged so that each metered dose or "puff" of aerosol contains 20 μg to 1000 μg of the compound of the invention. The overall daily does with an aerosol will be within the range 100 μg to 10 mg. Administration may be several times daily, for example 2, 3, 4 or 8 times, giving for example, 1, 2 or 3 doses each time.

The following Examples illustrate the preparation of the compounds of the present invention. Commercial reagents were utilized without further purification. Chromatography refers to column chromatography preformed using 32–63 μm silica gel and executed under nitrogen pressure (flash chromatography) conditions. Room temperature refers to 20–25° C.

EXAMPLE 1

General Procedure for the Coupling of Amino Acid Derivatives with 5-Aminoindole Derivatives To a stirred mixture of the N-protected amino acid (1.1 mmol, 1.4 eq) in anhydrous methylene chloride (5 mL) was added carbonyl diimidazole (180 mg, 1.4 mmol, 1.1 eq). The reaction mixture was stirred at room temperature under nitrogen until the reaction solution became clear (15 minutes to 24 hours, depending on the substrate), at which time the appropriate 5-aminoindole derivative (0.80 mmol) was directly added to the reaction solution. The resulting reaction solution was stirred at room temperature under nitrogen for 2 hours, and then it was directly chromatographed using silica gel (approximately 20 g) and elution with CH$_2$Cl$_2$/CH$_3$OH/triethylamine [8:1:1] to afford the coupled amino acid/5-amino indole derivative.

Using this procedure, the following compounds were prepared.

A.  5-(N-Benzyloxycarbonylglycyl)amino-3-(N-methylpyrrolidin- 2R-ylmethyl)-1H-indole N-Benzyloxycarbonylglycine and 5-amino-3-(N-methylpyrrolidin- 2R-ylmethyl)-1H-indole were used. Chromatography as described above afforded the title compound as a clear, pale red foam (74%): R$_f$=0.3 in CH$_2$Cl$_2$/CH$_3$OH/triethylamine [8:1:1]; ¹H NMR (CDCl$_3$) δ9.25 (br s, NH), 9.08 (br s, NH), 7.69 (s, 1H), 7.28 (br s, 5H), 7.12 (d, J=8.8 Hz, 1H), 7.08 (d, J=9.3Hz, 1H), 6.88 (br s, 1H), 6.32 (br t, NH), 5.09 (s, 2H), 3.99 (br d, J=4.8Hz, 2H), 3.07–3.00 (m, 2H), 2.56–2.36 (m, 2H), 2.36 (s, 3H), 2.16 (dd, J=8.7 and 17.3 Hz, 1H), 1.76–1.44 (m, 4H); LRMS (m/z, relative intensity) 420 (2), 418 (22), 310 (4), 228 (4), 171 (13), 108 (25), 84 (100); HRMS calculated for C$_{24}$H$_{28}$N$_4$O$_3$ 420.216, found 420,208.

B. 5-(N-benzyloxylcarbonyl-S-histidyl) amino-3-(N-methylpyrrolidin- 2R-ylmethyl),1H-indole N-Benzyloxycarbonyl-S-histidine and 5-amino-3-(N-methylpyrrolidin- 2R-ylmethyl)-1H-indole were used. Chromatography as described above afforded the title compound (46% ) as an pale yellow foam: $R_f$=0.4 in $CH_2Cl_2/CH_3OH/$ ammonium hydroxide [8:2:0.1]; $^{13}C$ NMR ($CD_3OD$) δ172.3, 158.3, 138.1, 136.2, 135.7, 130.7, 129.5, 129.0, 128.8, 128.6, 124.8, 117.3, 113.4, 112.3, 68.4, 67.7, 58.3, 57.3, 40.9, 32.2, 31.2, 30.2, 22.4; FAB LRMS (m/z, relative intensity) 501 ([MH$^+$], 100), 417 (4), 367 (6), 309 (4), 273 (6). Anal. calcd for $C_{28}H_{32}N_6O_3$. 0.25$H_2O$; C, 66.58; H, 6.49; N, 16.63. Found: 66.47; H, 6.56; N, 16.48.

C. 5-N-benzyloxylcarbonyl-S-alanyl)amino-3-N-methylprrolidin- 2R-ylmethyl)-1H-indole N-Benzyloxycarbonyl-S-alanine and 5-amino-3-(N-methylpyrrolidin- 2R-ylmethyl)-1H-indole were used. Chromatography as described above afforded the title compound (33%) as a white foam: $R_f$=0 in $CH_2Cl_2/CH_3OH$/ammonium hydroxide [9:1:0.1]; $^{13}C$ NMR ($CDCl_3$) δ177.9, 155.9, 138.6, 136.8, 131.4, 128.4, 127.9, 127.6, 124.0, 113.3, 112.3, 109.1, 103.5, 68.6, 66.4, 56.1, 51.3, 39.7, 30.4, 26.4, 21.4, 19.4. Anal. calcd for $C_{25}H_{30}N_4O_3$. 0.5 ethyl acetate $[C_4H_8O_2]$. 0.5 methylene chloride $[CH_2Cl_2]$: C, 63.42; H, 6.77; N, 10.75. Found: C, 63.45; H, 6.72; N, 10.79.

D. 5-N-benzyloxylcarbonyl-S-phenylalanyl)amino-3-N-methylpyrrolidin- 2R-ylmethyl)1H-indole N-Benzyloxycarbonyl-S-phenylalanine and 5-amino-3-(N-methylpyrrolidin-2R-ylmethyl)-1H-indole were used. Chromatography as described above afforded the title compound (90%) as a white foam: $R_f$=0.7 in $CH_2Cl_2/CH_3OH/$ ammonium hydroxide [9:1:0.1]; $^{13}C$ NMR ($CDCl_3$) δ169.4, 156.2, 136.6, 136.1, 134.0, 129.4, 129.0, 128.7, 128.5, 128.2, 128.0, 127.6, 127.0, 123.4, 116.5, 113.6, 111.4, 111.3, 67.1, 66.6, 57.4, 57.1, 40.7, 39.1, 31.4, 29.6, 21.8; FAB LRMS (m/z, relative intensity) 511 ([MH$^+$], 77), 281 (11), 147 (100); HRMS calculated for $[C_{31}H_{34}N_4O_3$.H]$^+$511.2712, found 511.2687. Anal. calcd for $C_{31}H_{34}N_4O_3$. 0.75$H_2O$: C, 71.04; H, 6.83; N, 10.69. Found: C, 71.20; H, 6.88; N, 10.72.

EXAMPLE 2

General Procedure for the Alkylation of 5-Amino-(R)-3-(pyrrolidin- 2-ylmethyl)-1H-indole Forming 5-Amino-(R)-3-(N-alkylpyrrolidin-2-ylmethyl)-1H-indoles To a stirred solution of 5-amino-(R)-3-(pyrrolidin- 2-ylmethyl)-1H-indole (1.00 mmol) and triethylamine (0.126 g, 1.25 mmol, 1.25 eq) in either anhydrous methylene chloride, anhydrous acetonitrile, absolute ethanol, or i-propanol (10 mL) at room temperature under nitrogen is added dropwise the alkylating agent (1.25 mmol). The resulting reaction solution is then stirred under nitrogen at room temperature for 1 to 20 hours, depending on substrate. The resulting reaction mixture is directly column chromatographed using silica gel (approximately 25 g) and elution with methylene chloride; methanol: ammonium hydroxide [9:1:0.1] to afford the 5-amino-(R)-3-(N-alkylpyrrolidin-2-ylmethyl)-1H-indole.

EXAMPLE 3

(R)-5-Amino-3-(pyrrolidin-2-ylmethyl)-1H-indole

A mixture of (R)-3-(N-benzyloxycarbonylpyrrolidin-2-ylmethyl)- 5-dibenzylamino-1H-indole (7.90 g, 14.91 mmol) and moist palladium (II) hydroxide on carbon (Pearlman's catalyst, 3.16 g) in absolute ethanol (100 mL) was shaken under a hydrogen atmosphere (3 atm) for 12 hours at room temperature. The resulting mixture was filtered through diatomaceous earth, and the filtrate was evaporated and dried under reduced pressure to afford the title compound as a white foam (3.20 g, 100%): $^1H$ NMR ($CD_3OD$) δ7.18 (d, J=8.5 Hz, 1H), 7.08 (s, 1H), 6.92 (d, J=2.0 Hz, 1H), 6.69 (dd, J=1.9 and 8.5 Hz, 1H), 3.81–3.69 (m, 1H), 3.30–2.95 (m, 4H), 2.09–1.55 (m, 4H); $^{13}C$ NMR ($CD_3OD$) δ140.1, 133.4, 129.1, 125.0, 114.6, 113.1, 109.8, 105.1, 62.1, 46.0, 31.1, 29.1, 24.3; LRMS (m/z, relative intensity) 215 (M$^+$, 2), 198 (1) , 146 (100), 128 (7), 117 (9), 70 (60).

EXAMPLE 4

(R)-3-(N-Benzyloxycarbonylpyrrolidin-2-ylmethyl)-5-dibenzylamino- 1H-indole

To a stirred solution of (R)-3-(N-benzyloxycarbonylpyrrolidin- 2-ylcarbonyl)-5-dibenzylamino-1H-indole (1.50 g, 2.75 mmol) in anhydrous tetrahydrofuran (30 mL) was added lithium borohydride (0.24 g, 11.0 mmol, 4.0 eq) as a solid. The resulting reaction mixture was heated at reflux for 4 hours. A saturated solution of sodium hydrogen carbonate (10 mL) was then added, and this mixture was stirred at room temperature for 30 minutes. This aqueous mixture was then extracted with ethyl acetate (3×25 mL), and the organic extracts were combined, dried ($MgSO_4$), and evaporated under reduced pressure. Column chromatography of the residue using silica gel (approximately 50 g) and elution with ethyl acetate/hexanes [1:3] afforded the title compound (1.02 g, 70%) as a white foam: FAB LRMS (m/z, relative intensity) 530 (MH$^+$, 87), 529 (M$^+$, 100), 439 (10), 409 (10), 325 (32), 235 (20).

EXAMPLE 5

(R)-3-N-Benzyloxycarbonylpyrrolidin-2-ylcarbonyl)-5-dibenzylamino-1H-indole

To a stirred mixture of (R)-N-carbobenzyloxyproline (3.59 g, 14.41 mmol) and N,N-dimethylformamide (0.1 mL) in methylene chloride (45 mL) was added dropwise oxalyl chloride (1.87 mL, 21.62 mmol, 1.5 eq). The resulting effervescing mixture was stirred at room temperature under nitrogen for 1.5 hours. The reaction solution was then evaporated under reduced pressure, yielding the residue [(R)-N-carbobenzyloxyproline acid chloride] which was dissolved in anhydrous ether (50 mL). This solution was added dropwise to a stirred, preformed solution of 5-dibenzylaminoindole (9.00 g, 28.81 mmol, 2.0 eq) and ethyl magnesium bromide (3.0M in ether, 10.08 mL, 30.25 mmol, 2.1 eq) in anhydrous ether (75 mL), which had been stirring at room temperature under nitrogen for 30 minutes prior to the addition of the ethereal solution of the (R)-N-carbobenzyloxyproline acid chloride. The resulting reaction mixture was stirred at room temperature under nitrogen for 30 minutes, and then ethyl acetate (100 mL) and a saturated solution of sodium hydrogen carbonate (75 mL) were added. The organic layer was removed, and the aqueous layer was extracted with ethyl acetate (100 mL). The organic extracts were combined, dried ($MgSO_4$), and evaporated under reduced pressure to afford a green oil. Trituration of this oil in anhydrous ether (50 mL) afforded the title compound as a white solid (3.20 g, 21%): m.p., 176.0°–177.0° C; LRMS (m/z, relative intensity) 543 (100, M$^+$), 453 (10), 407 (7), 339 (40) , 307 (10) , 247 (10) , 154 (38); $[α]^{25}$=+112° (tetrahydrofuran (THF), c=1.0); Anal. calcd. for $C_{35}H_{33}N_3O_3$: C, 77.32; H, 6.12; N, 7.73. Found: C, 77.35; H, 6.30; N, 7.66.

EXAMPLE 6

(R)-5-Amino-3-(N-methylpyrrolidin-2-ylmethyl)-1H-indole

A mixture of (R)-5-dibenzylamino-3-(N-methylpyrrolidin-2-ylmethyl)-1H-indole (1.08 g, 2.64 mmol) and palladium [II] hydroxide on carbon (0.6 g) in absolute ethanol (25 mL) was shaken under a hydrogen atmosphere (3 atm) at 40° C. for 4 hours. The resulting mixture was filtered through diatomaceous earth, and the filtrate was evaporated under reduced pressure to afford the title compound (0.60 g, 2.62 mmol, 99%) as a white foam: $^1$H NMR (DMSO-$d_6$) $\delta$10.65 (br s, NH), 7.14 (d, J=2.2 Hz, 1H), 7.12 (d, J=8.6 Hz, 1H), 6.85 (d, J=1.6 Hz, 1H), 6.60 (dd, J=2.0 and 8.6 Hz, 1H), 3.63–2.83 (m, 7H), 2.78 (s, 3H), 2.05–1.67 (m, 4H); $[\alpha]^{25}$= +9° (MeOH, c=1.0); HEMS calculated for $C_{14}H_{19}N_3$: 229.1575; found: 229.1593.

EXAMPLE 7

(R)-5-Dibenzylamino-3-(N-methylpyrrolidin-2-ylmethyl)-1H-indole

To a stirred mixture of lithium aluminum hydride (0.96 g, 25.2 mmol, 2.0 eq) in anhydrous tetrahydrofuran (125 mL) at 0° C. was added dropwise a solution of (R)-3-(N-benzyloxycarbonylpyrrolidin-2-ylcarbonyl)-5-dibenzylamino-1H-indole (6.90 g, 12.69 mmol) in anhydrous tetrahydrofuran (25mL). The resulting reaction mixture was stirred at room temperature under nitrogen for 30 minutes. Lithium borohydride (0.55 g, 25.2 mmol, 2.0 eq) was then added, and the reaction mixture was heated at reflux (66° C.) under nitrogen for 6 hours. The reaction mixture was cooled, and water (1.5 mL), a solution of sodium hydroxide (20%, 1.5 mL), and more water (4.5 mL) were added, sequentially. The resulting mixture was stirred at room temperature under nitrogen for 1 hour, filtered through diatomaceous earth, and the filtrate was evaporated under reduced pressure to yield a green oil (8.8 g). This oil was dissolved in absolute ethanol (90 mL), and cesium carbonate (8.0 g) and sodium carbonate (8.0 g) were added. The resulting mixture was heated at reflux for 12 hours. The reaction mixture was then evaporated under reduced pressure, and the residue was partitioned between a saturated solution of sodium hydrogen carbonate (50 mL) and ethyl acetate (100 mL). The organic layer was removed, and the aqueous layer was extracted with ethyl acetate (100 mL). The organic extracts were combined, dried (MgSO$_4$), and evaporated under reduced pressure to afford a brown oil. Column chromatography of this oil using silica gel (approximately 200 g) and elution with methylene chloride/methanol/ammonium hydroxide [9:1:0.1] afforded the title compound (4.63 g, 89%) as a pale green foam: $^1$H NMR (CDCl$_3$) $\delta$7.82 (br s, NH), 7.35–7.19 (m, 10H), 7.20 (d, J=8.6 Hz, 1H), 6.95 (d, J=2.1 Hz, 1H), 6.85 (dd, J=2.3 and 8.7 Hz, 1H), 6.80 (d, J=2.2 Hz, 1H), 4.65 (s, 4H), 3.25–3.02 (m, 2H), 2.52 (dd, J=9.5 and 13.9 Hz, 1H), 2.39–2.15 (m, 2H), 2.30 (s, 3H), 1.85–1.40 (m, 4H); $^{13}$C NMR (CDCl$_3$) $\delta$143.2, 139.7, 130.5, 128.5, 128.2, 127.3, 126.8, 122.9, 112.5, 112.2, 111.8, 103.4, 67.0, 57.4, 56.4, 40.6, 31.4, 29.7, 21.9; HRMS calculated for $C_{28}H_{31}N_3$ 409.2520, found 409.2475.

EXAMPLE 8

5-Dibenzylamino-1H-indole

To a stirred mixture of 5-aminoindole (3.00 g, 22.7 mmol) and triethylamine (10.5 mL, 74.9 mmol, 3.3 eq.) in acetonitrile (30 mL) at room temperature under nitrogen was added benzyl bromide (8.2 mL, 68.9 mmol, 3.0 eq.) dropwise. The resulting reaction mixture was heated at reflux under nitrogen for 3 hours. The resulting reaction mixture was filtered, and the filtrate was evaporated under reduced pressure. Column chromatography of the residue using silica gel (approximately 200 g) and elution with ethyl acetate/hexanes [gradient 1:9 to 1:1] afforded the title compound as an off white solid (6.19 g, 87%): m.p., 124.0°–126.0° C.; $^{13}$C NMR (acetone-$d_6$) $\delta$144.3, 140.8, 131.8, 129.9, 129.2, 128.3, 127.5, 125.7, 113.5, 112.4, 106.4, 101.9, 57.0; TLC [15% ethyl acetate in hexanes]: R$_{0.3}$.

I claim:

1. A compound of the formula

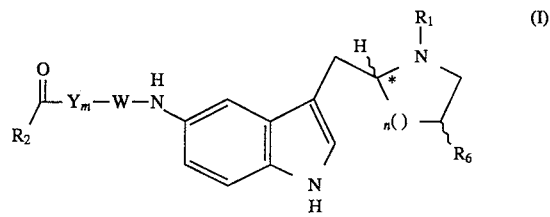

wherein n is 0, 1, or 2; m is 0 or 1; Y and W are each an amino acid residue; $R_1$ is hydrogen, $C_1$–$C_6$ alkyl, $C_3$–$C_6$ alkenyl, $C_3$–$C_6$ alkynyl, aryl, $C_1$–$C_3$ alkylaryl, or $C_1$–$C_3$ alkylheteroaryl, and —(CH$_2$)$_p$R$_3$; $R_2$ is CF$_3$, $C_1$–$C_6$ alkyl, aryl, $C_1$–$C_3$ alkylaryl, and —OR$_5$; $R_3$ is cyano, trifluoromethyl, or —OR$_4$; $R_4$ is hydrogen, $C_1$–$C_6$ alkyl, $C_1$–$C_3$ alkylaryl, or aryl; $R_5$ is $C_1$–$C_6$ alkyl, $C_1$–$C_3$ alkylaryl, or aryl; $R_6$ is hydrogen, —OR$_7$, or —NHCOR$_7$; $R_7$ is hydrogen, $C_1$ to $C_6$ alkyl, aryl, or $C_1$ to $C_3$ alkyl-aryl; p is 1, 2, or 3; a chiral carbon is designated by an asterisk; and the above aryl groups and the aryl moieties of the above alkyl-aryl groups are independently selected from phenyl and substituted phenyl, wherein said substituted phenyl may be substituted with one to three groups selected from $C_1$ to $C_4$ alkyl, halogen, hydroxy, cyano, carboxamide, nitro, and $C_1$ to $C_4$ alkoxy and the pharmaceutically acceptable salts thereof.

2. The compound of claim 1, wherein the compound of formula I is

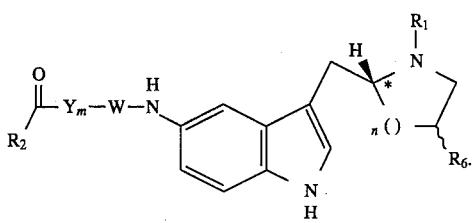

3. The compound of claim 2, wherein the compound is the cis epimer.

4. The compound of claim 1, wherein the amino acid is a naturally occurring amino acid.

5. The compound of claim 4, wherein the compound of formula I is

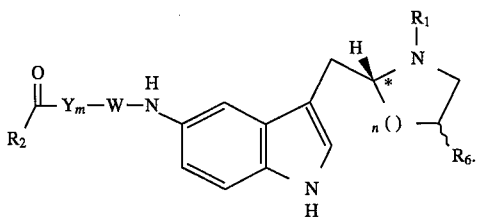

6. The compound of claim 5, wherein the compound is the cis epimer.

7. The compound of claim 4, wherein the naturally occurring amino acid is alanine, valine, leucine, isoleucine, proline, phenylalanine, tryptophan, methionine, glycine, serine, threonine, cysteine, tyrosine, asparginine, glutamine, aspartic acid, glutamic acid, lysine, arginine, or histidine.

8. The compound of claim 7, wherein the compound of formula I is

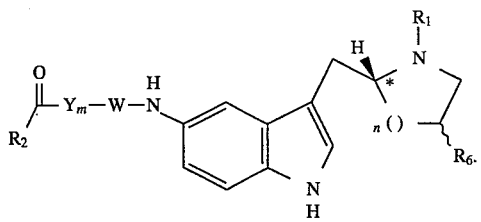

9. The compound of claim 8, wherein the compound is the cis epimer.

10. The compound of claim i wherein n is 1; m is 0; the amino acid is a naturally occurring amino acid; $R_1$ is hydrogen, $C_1$–$C_6$ alkyl, or $CH_2CH_2OCH_3$; $R_2$ is $C_1$–$C_4$ alkyl, phenyl —$CF_3$, or —$OR_5$.

11. The compound of claim 10, wherein the compound of formula I is

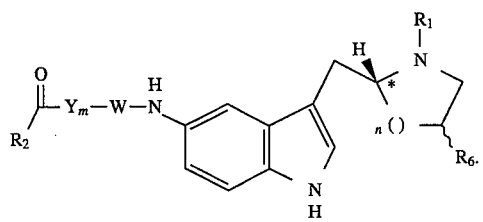

12. The compound of claim 11, wherein the compound is the cis epimer.

13. The compound of claim 10, wherein the naturally occurring amino acid is alanine, valine, leucine, isoleucine, proline, phenylalanine, tryptophan, methionine, glycine, serine, threonine, cysteine, tyrosine, asparginine, glutamine, aspartic acid, glutamic acid, lysine, arginine, or histidine.

14. The compound of claim 13, wherein the compound of formula I is

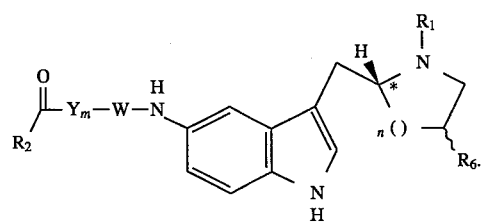

15. The compound of claim 14, wherein the compound is the cis epimer.

16. The compound of claim 1, said compound being selected from: 5-(N-benzyloxycarbonylglycyl)amino-3-(N-methylpyrrolidin- 2R-ylmethyl)-1H-indole; 5-(N-benzyloxycarbonyl-S-histidyl) amino-3-(N-methylpyrrolidin2R-ylmethyl)- 1H-indole; 5-(N-benzyloxycarbonyl-S-alanyl)amino-3-(N-methylpyrrolidin- 2R-ylmethyl)-1H-indole; and 5-(N-benzyloxycarbonyl-S-phenylalanyl) amino-3-(N-methylpyrrolidin-2R-ylmethyl)-1H-indole.

17. A pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an amount of a compound according to claim 1 effective in treating such condition and a pharmaceutically acceptable carrier.

18. A pharmaceutical composition for treating disorders arising from deficient serotonergic neurotransmission comprising an amount of a compound according to claim 1 effective in treating such a disorder and a pharmaceutically acceptable carrier.

19. A method for treating a condition selected from hypertension, depression, anxiety, eating disorders, obesity, drug abuse, cluster headache, migraine, pain, and chronic paroxysmal hemicrania and headache associated with vascular disorders comprising administering to a mammal requiring such treatment an amount of a compound according to claim 1 effective in treating such condition.

20. A method for treating disorders arising from deficient serotonergic neurotransmission comprising administering to a mammal requiring such treatment as amount of a compound according to claim 1 effective in treating such condition.

21. A compound of the formula

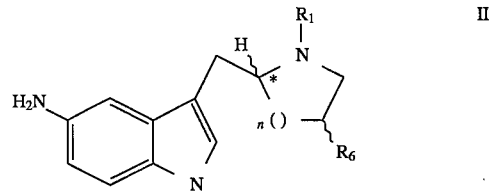

where n is 0, 1, or 2; $R_I$ is hydrogen, $C_1$–$C_6$ alkyl, $C_3$–$C_6$ alkenyl, $C_3$–$C_6$ alkynyl, aryl, $C_1$–$C_3$ alkylaryl, or $C_1$–$C_3$ alkylheteroaryl, and —$(CH_2)_pR_3$; $R_3$ is cyano, trifluoromethyl, or —$OR_4$; $R_4$ is hydrogen, $C_1$–$C_6$ alkyl, $C_1$–$C_3$ alkylaryl, or aryl; $R_6$ is hydrogen, —$OR_7$, or —$NHCOR_7$; $R_7$ is hydrogen, $C_1$ to $C_6$ alkyl, aryl, or $C_1$ to $C_3$ alkyl-aryl; p is 1, 2, or 3; and the above aryl groups and the aryl moieties of the above alkylaryl groups are independently selected from phenyl and substituted phenyl, wherein said substituted phenyl may be substituted with one to three groups selected from $C_1$ to $C_4$ alkyl, halogen, hydroxy, cyano, carboxamide, nitro, and $C_1$ to $C_4$ alkoxy.

22. The compound of claim 21, wherein the compound of formula II is

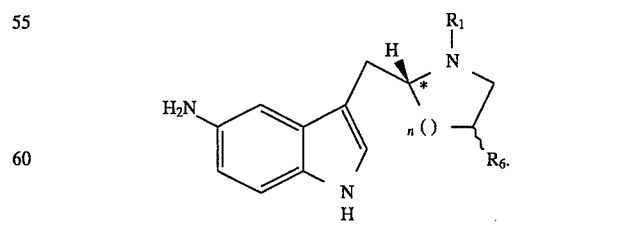

23. The compound of claim 22, wherein the compound is the cis epimer.

* * * * *